United States Patent [19]
Zastrow et al.

[11] Patent Number: 5,919,490
[45] Date of Patent: *Jul. 6, 1999

[54] PREPARATION FOR IMPROVING THE BLOOD SUPPLY CONTAINING HARD MAGNETIC PARTICLES

[75] Inventors: Leonhard Zastrow, Monaco, Monaco; Dagmar Hülsenberg, Ilmenau; Karin Golz, Berlin, both of Germany; Klaus Stanzl, White Plains, N.Y.

[73] Assignee: Lancaster Group GmbH, Ludwigshafen, Germany

[ * ] Notice: This patent is subject to a terminal disclaimer.

[21] Appl. No.: 08/951,701

[22] Filed: Oct. 16, 1997

Related U.S. Application Data

[63] Continuation-in-part of application No. 08/522,304, filed as application No. PCT/DE94/00879, Jul. 19, 1994, Pat. No. 5,800,835.

[30] Foreign Application Priority Data

Jul. 19, 1993 [DE] Germany .............................. 43 25 071

[51] Int. Cl.⁶ .................................................. A61K 31/715
[52] U.S. Cl. ............................................................ 424/647
[58] Field of Search ...................... 424/647, 648

[56] References Cited

U.S. PATENT DOCUMENTS 4,335,094  6/1982  Mosbach .
4,501,726  2/1985  Schröder et al. .
5,039,559  8/1991  Sang et al. .
5,411,730  5/1995  Kirpotin et al. ......................... 424/647

FOREIGN PATENT DOCUMENTS 4108710  7/1992  Japan .

OTHER PUBLICATIONS

Beauty Forum, Feb. 1993, S. 46.

Derwent Abstracts, EP 186,616 A–86–171,075/27, J 59116214 A–84203893/33, J 59139314 A–84–2339/38, and JO 209428 A–90–110377/15.

*Primary Examiner*—James H. Reamer
*Attorney, Agent, or Firm*—Collard & Roe, P.C.

[57] ABSTRACT

A preparation for stimulating the blood circulation of the skin comprising a dispersion containing a proportion of finely divided magnetically hard single-domain particles in the dispersion being in the range from 0.01% to 70% by weight, based on the total weight of the dispersion; these particles having a strong coercive field and being in the range 600 to 1200 nm; and the magnetically hard single-domain particles are selected from the group consisting of barium hexaferrite, strontium hexaferrite, undoped barium hexaferrite, undoped strontium hexaferrite, and the mixtures thereof; and the balance up to 100% by weight of a cosmetic or pharmaceutical excipient carrier substance or a pharmaceutical additive, based on the total weight of the dispersion.

10 Claims, 1 Drawing Sheet

PREPARATION FOR IMPROVING THE BLOOD SUPPLY CONTAINING HARD MAGNETIC PARTICLES

CROSS-REFERENCE TO RELATED APPLICATION

This is a continuation-in-part patent application of parent U.S. patent application Ser. No. 08/522,304 filed Sep. 5, 1995 now U.S. Pat. No. 5,800,835, which is a 371 of PCT/DE94/00879 filed Jul. 19, 1994.

BACKGROUND OF THE INVENTION

1. Field of the Invention

The present invention relates to a preparation for stimulating the circulation of blood.

2. The Prior Art

Stimulation of the blood circulation in the skin is a problem for which a solution has been sought. A number of research results have already been disclosed, and different research paths have been followed. The influence of magnetic forces has also been increasingly studied, especially in recent years.

Among other things, the use of pulsed electromagnetic fields has been studied as a potentially useful therapy for the postoperative treatment of pain and oedema (Mayrovitz, HJ. N., Larsen, P. B. *WOUNDS,* Vol. 4, no. 5, 197 (1992)).

*Beauty Forum,* 2/93, page 46, has disclosed the use of a stick shaped magnet which the user rubs over the skin, such that the resulting magnetic field will have an effect on the skin surface. According to the manufacturer, cells which are no longer fully functional are supposed to be stimulated by a magnetic field, initiating a self-healing process and restoring firmness and elasticity to the skin.

The use of magnetic polymer particles, some of which have pharmacologically active compounds coupled to them, has also been described, e.g., in U.S. Pat. Nos. 4,501,726, 4,335,094, and 5,039,559. In these patent descriptions, soft ferrite particles or ferroaluminates were encapsulated with polymeric materials and introduced into the body.

A magnetic cosmetic preparation is described in JPA 4,108,710 (Yoko Shiga). Here, ferromagnetic substances, e.g. magnetite or manganese zinc ferrite (all soft ferrites), are dispersed in a cosmetic preparation in the demagnetized state and the preparation is magnetized after cosmetic application to the skin. This form of application is said to have a circulation-stimulating effect, namely a 3.4% increase in circulation in animal experiments with a proportion of 0.1% of magnetite. This prior art document contains no further information.

SUMMARY OF THE INVENTION

It is an object of the invention to provide a novel preparation with a substantially improved circulation-stimulating effect. According to the invention, the preparation for stimulating the circulation contains a pharmaceutically or cosmetically acceptable excipient and optionally conventional formulation additives, in which there are finely divided, magnetically hard single-domain particles with a strong coercive field and with sizes in the range 600 to 1200 nm.

The term "single-domain particles" is understood as meaning single crystals of naturally uniform magnetic orientation. Magnetically hard single-domain particles which are particularly preferred in the present invention are barium or strontium hexaferrites, which advantageously are not doped. These undoped barium or strontium hexaferrites are prepared by known processes, e.g. by growing single crystals from a tempered glass melt in accordance with the glass crystallization technique. A suitable glass for this purpose is the three-component system $BaO-Fe_2O_3-B_2O_3$, which is advantageously composed of 20% to 50% by weight of $Fe_2O_3$, 30% to 50% by weight of BaO and 20% to 50% by weight of $B_2O_3$.

The diameter/thickness ratio of the crystals of barium hexaferrite or strontium hexaferrite is generally 3:1 to 10:1.

The sizes of the single-domain particles are preferably in the range 750 to 1000 nm and especially in the range 800 to 950 nm. In this range, the particles have a particularly advantageous, strong coercive field. The coercive field is advantageously in the range 3000 to 5000 Oersted and preferably in the range 4000 to 5000 oersted, although it can also be higher.

The single-domain particles according to the invention can be readily dispersed in a pharmaceutically/cosmetically acceptable excipient and in additives by the conventional processes and there is only insignificant aggregation, if any, in the dispersion. This is particularly surprising because it is clear from all the publications of the state of the art that permanent-magnetic particles, i.e, magnetically hard particles, always tend to aggregate. Therefore these particles have to be incorporated into a dispersion with particular organic polymers or inorganic substances. These inorganic or organic additives function as a barrier substance in which the magnetically hard particles are embedded, or they function as a result of coupling to these additives, thereby avoiding aggregation. This is not necessary in the present invention and the magnetically hard single-domain particles alone, especially the barium or strontium hexaferrites prepared by the glass crystallization technique, give a dispersion which readily produces a stable dispersion with the optional addition of certain dispersants.

The novel preparations exhibit an excellent circulation-stimulating action. With the aid of conventional cosmetic or dermatological excipients, for example, they can be processed into a composition for application to the skin. Also, they can be converted into enteral or parenteral processing forms by conventional techniques and with the conventional excipient systems. When used on the skin, the redness or skin and eye irritation occurring for example with the medicinal use of conventional vasodilators are avoided. This represents an appreciable advantage in the practical application of dermatological preparations. The circulation-stimulating action also accounts for the observation of a stimulating activity on hair growth at appropriate concentrations.

The proportion of magnetically hard single-domain particles according to the invention in the dispersion is generally in the range 0.01% to 70% by weight, preferably in the range 0.01% to 15% by weight and especially in the range 0.01% to 10% by weight, based on the total weight of the dispersion.

According to the invention, it is particularly advantageous for dermal/cosmetic application if the magnetically hard single-domain particles are present in combination with asymmetric lamellar aggregates consisting of phospholipids with a phosphatidylcholine content in the range 30% to 99% by weight and oxygen-charged fluorocarbons in the range 0.2% to 100% (weight/volume), according to DE 4,221,255, to which reference is made. Here the asymmetric lamellar aggregates penetrate the skin as a function of critical solubility temperatures of the fluorocarbons or fluorocarbon mixtures used. Such a combination has an additive effect and in some cases a synergistic effect on the supply of oxygen to the skin. With the aid of the asymmetric lamellar aggregates, the magnetically hard single-domain particles are introduced in encapsulated form onto the surface of the skin. By virtue of their magnetic force, they exert a suction effect on the haemoglobin particles present in the blood, which are "pulled" onto the tips of the furthest blood capillaries. This increases the supply of oxygen to the skin, which is boosted further by the oxygen brought into the skin from outside with the aid of the asymmetric lamellar aggregates.

The phospholipids used for the asymmetric lamellar aggregates are advantageously selected from the group consisting of natural phospholipids, such as soya lecithin and egg lecithin, as well as synthetic phospholipids and/or partially hydrogenated phospholipids.

It is particularly advantageous if the lipid fraction used contains very high proportions of phosphatidylcholine, especially proportions of 70% to 99% by weight. In addition to phosphatidylcholine, lysolecithin can also be present in the concentration range 1% to 10% by weight.

To achieve a slower penetration of the skin, the composition can contain fluorocarbons or fluorocarbon mixtures with a higher critical solubility temperature.

The term "fluorocarbons" used here is understood as meaning perfluoroinated or highly fluorinated carbon compounds or mixtures which are capable of transporting gases such as oxygen and carbon dioxide. In terms of this invention, highly fluorinated hydrocarbon compounds are those in which most of the hydrogen atoms have been replaced with fluorine atoms, so further replacement does not necessarily increase the ability to transport gases. This is usually achieved when up to about 90% of the hydrogen atoms have been replaced with fluorine atoms. In terms of the present invention, preferred fluorine atoms are those in which at least 95% of the hydrogen atoms, preferably 98% and particularly preferably 100%, have been replaced.

A large number of fluorocarbons can be used, e.g., linear and branched aliphatic fluoroalkanes, monocylic or bicylic and optionally fluoroalkyl-substituted fluorocycloalkanes, perfluoroinated aliphatic or bicyclic amines, bis (perfluoroalkyl)ethenes, perfluoroinated polyethers or mixtures thereof. Examples of particularly preferred fluorocarbons are perfluorodecalin, F-butyltetrahydrofuran, perfluorotributylamine, perfluorooctylbromide, bisfluoro (butyl)ethene or bisfluoro(hexyl)ethene or $C_6$ to $C_9$-perfluoroalkanes.

As already stated, it is also possible to use, in addition to phosphatidylcholine, lysolecithins and/or charged phospholipids such as phosphatidylethanolamine, n-acetylphosphatidylethanolamine or phosphatidic acid, in the concentration range 0.1% to 30% by weight.

If desired, the magnetically hard single-domain particles can be coated with a layer which only slightly reduces the coercive field but prevents or inhibits the escape of barium and/or strontium ions. This can be necessary when there is a need only to use preparations from which the leaching of barium or strontium ions over a particular period of time is to be avoided as a requirement of the health authority. Examples of substances suitable for this purpose are inorganic substances such as titanium dioxide, zirconium dioxide or hydroxyapatite. Other substances can also be used, however, provided they fulfil the same function, i.e., that of keeping the escape of barium or strontium ions, by boiling with hydrochloric acid over a period of thirty minutes, below the permitted value.

The present invention further relates to a process for the manufacture of the preparation, comprising dispersing the magnetic single-domain particles, with the optional addition of a dispersant, in a conventional excipient for pharmaceutical or cosmetic preparations, and optionally other additives, by using devices with a shear action or an ultrasonic action. This dispersing occurs at speeds of rotation in the range of 10,000 to 27,000 rpm, with the size of the magnetically hard single-domain particles produced being in the range of 600 to 1200 nm. Surprisingly, this gives a stable dispersion without the formation of aggregates normally to be expected, and thereby avoids agglomeration of the end product. This is important for cosmetic/dermatological application and necessary for parenteral administration, e.g. intravenous administration, in order to ensure a stable colloid-disperse system. The processing necessary for the latter form of administration, e.g. with polymeric substances, is avoided according to the invention.

In the case where the magnetically hard single-domain particles according to the invention are to be combined with asymmetric lamellar aggregates, the asymmetric lamellar aggregates are prepared first by the pre-emulsification of fluorocarbons in an aqueous phospholipid solution at about 12,000 to 15,000 rpm.

This is followed by high-pressure homogenization with the magnetically hard single-domain particles to produce appropriate spherical lamellar structures. To avoid autoxidation processes in the unsaturated acid radical of native lipids, it is possible to add antioxidants, a.g. α-tocopherol. The fluorocarbon content and hence the oxygen availability can be varied within wide limits.

The invention further relates to the use of a pharmaceutical or cosmetic preparation for stimulating the circulation, wherein a form of administration for a pharmaceutical or cosmetic preparation, comprises an excipient and optionally other additives, in which there are finely divided, magnetically hard single-domain particles with a strong coercive field and with sizes in the range 600 to 1200 nm, is introduced into the body or applied to the skin. The action in terms of stimulation of the circulation is determined here by the amount of single-domain particles, which penetrate the skin, e.g., in the case of cosmetic/dermal use and create a corresponding magnetic field therein. Utilization of the magnetic properties of the blood for improving the blood circulation, especially in the fine capillaries, results in an improved supply of oxygen, an improved supply of nutrients and an improved removal of waste products. This leads to a remission of skin wrinkles due to old age, an improved elasticity for the skin, a rejuvenation of the skin and, in the case of cellulitis, a substantially improved clinical picture. A stimulating action on hair growth is also in evidence.

Measurements under constant physiological conditions show that an increase in the microcirculation of up to 200% could be achieved. Microcirculation is understood as meaning the circulation in the capillary region of the skin. This result proves the superiority of the preparations according to the invention compared with the previous results of the state of the art.

An additional effect can be achieved in the case of pharmaceutical preparations, e.g., dermatological preparations, by the incorporation of desired drugs. This can be carried out in conventional manner, but particularly advantageously for example by including these pharmaceutically active compounds, together with the magnetically hard single-domain particles, in the asymmetric lamellar aggregates, thereby ensuring deep penetration into the skin.

Suitable pharmaceutically active compounds are pharmacological active ingredients in the form of systemic active ingredients, including cytostatic agents, carcinostatic agents, immunomodulators and vaccines, especially those of the following group: dermatological active ingredients, for example virustatic agents or virucidal medicinal agents, antimycotic agents, heparins (e.g., heparin calcium, heparin sodium, low-molecular heparins), antibiotics, corticoids, anti-infective agents, active ingredients for acne, local anesthetics, antiphlogistics, antihistamines or antipsoriatics; systemic active ingredients, for example non-steroidal analgesics/antirheumatics (e.g., diclofenac sodium, diclofenac diethylamine salt, etofenamate, flufenamic acid, 2-hydroxyethyl salicylate, ibuprofen, indomethacin, piroxicam), opiate receptor agonists and antagonists (e.g., buprenorphin, fentanyl, pentazocine, pethidine, tilidine, tramadol, naloxone), histamine antagonists (e.g., bamipine lactate, chlorphenoxamine hydrochloride, clemastine hydrogenfumarate, dimethindene maleate, pheniramine hydrogenmaleate), insulins, regulatory peptides and their inhibitors (e.g., anterior pituitary hormones and their inhibitors, posterior pituitary hormones, hypothalamic hormones) or sedatives/hypnotics (e.g., diazepam); and active ingredients of the group comprising cytostatic agents, carcinostatic agents, immunomodulators and vaccines.

A preferred dermatological active ingredient is, for example, rosmaric acid or another virucidal or virustatic active ingredient occurring in plants. A preferred systemic active ingredient is, for example, a low-molecular or high-molecular heparin, an oligopeptide or a polypeptide.

Other preferred active ingredients are vitamins (E, A, B, C), muramylpeptides, doxorubicin, gentamycin, gramicidin, dexamethasone, hydrocortisone, progesterone, prednisolone or derivatives thereof and/or acid or base addition salts derived therefrom, and also melanin.

With relative active ingredients and active ingredient combinations and for appropriate indications, antineoplastic therapy and antimicrobial and antiviral therapy are possible, as are other types of therapy which, as a result of the improved oxygen supply to the skin by virtue of the preparation according to the invention, also lead to an improved absorption of the pharmaceutical active ingredients and hence are more successful.

The amounts of active ingredient in therapeutic terms are generally very small, so that, for example, for the case of soluble active ingredients, solubilities of 0.5 to 12 g/100 ml are sufficient for medicinal use. If these solubilities are not attained, it is also possible to form an emulsion through the interaction of e.g., fluorocarbon and phospholipid, using known methods, in order to obtain the appropriate galenical composition. The active ingredients can therefore be incorporated into the novel excipient in the amount which is adequate in terms of current medical practice.

Excipients which can be used for the magnetically hard single-domain particles in a cosmetic preparation are the substances conventionally used for soaps, creams, lotions, emulsions, colognes, extracts, pastes, gels, powders and tinctures, it is also being possible, where appropriate, for these to be in the form of a dressing, plaster or spray.

BRIEF DESCRIPTION OF THE DRAWINGS

Other objects and features of the present invention will become apparent from the following detailed description considered in connection with the accompanying drawing which discloses embodiments of the present invention. It should be understood, however, that the drawing is designed for the purpose of illustration only and not as a definition of the limits of the invention.

In the drawing.

DETAILED DESCRIPTION OF PREFERRED EMBODIMENTS

Figure 1:
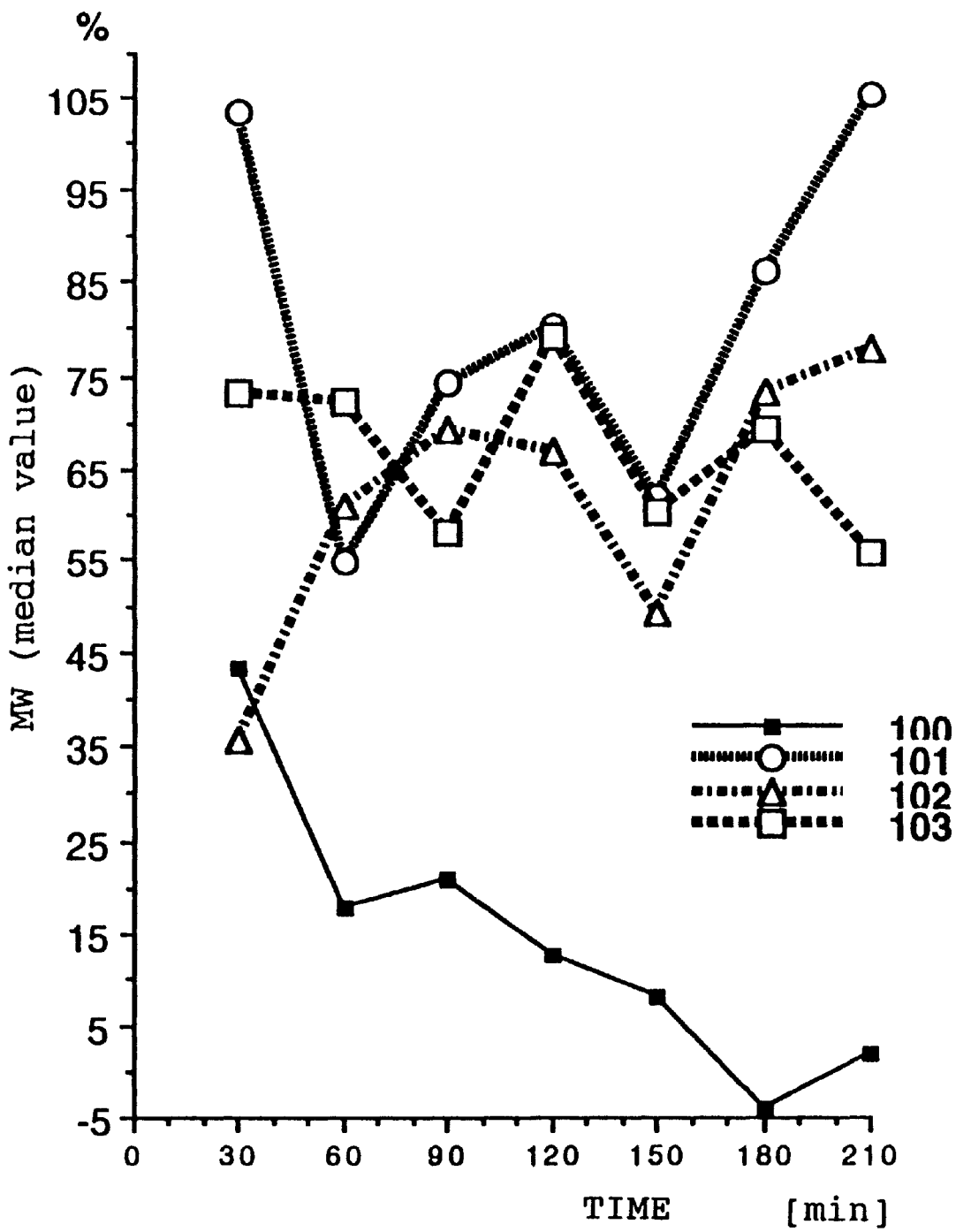
FIG. 1 is a graphical representation of the microcirculation with time for various test samples.

In the following Examples, all percents are by weight and are based upon the total composition weight.

EXAMPLE 1

Preparation of a Suspension With Magnetically Hard Strontium Hexaferrite Powders 5 percent by weight of magnetically hard strontium hexaferrite powder in a thickness ratio of 5:1 and in the particle size range 700–1000 nm are added to a mixture of propylene glycol, glycerol and distilled water in proportions of 1:1:2 and the whole is homogenized using a Turrax homogenizer at 15,000 rpm for a period of 30 min.

EXAMPLE 2

Preparation of a Suspension With Magnetically Hard Barium Hexaferrite Powders

15% by weight of magnetically hard barium hexaferrite powder in a thickness ration of 10:1 and in the particle size range 600–800 nm are added to a mixture of propylene glycol and distilled water in proportions of 1:1 and the whole is homogenized.

| Ultrasonic disintegrator | 400 W |
|---|---|
| Amplitude: | 50 |
| Time: | 40 min. |

EXAMPLE 3

Preparation of a Suspension With Magnetically Hard Barium Hexaferrite and Strontium Hexaferrite Powders 30% by weight of barium hexaferrite and strontium hexaferrite in proportions of 1:1 are added to a mixture of propylene glycol and distilled water in proportions of 1:1. The thickness ratios of the strontium ferrite and barium ferrite are 4:1 and 5:1 respectively. The particle size spectrum tolerates between 700 and 1000 nm.

| Homogenization parameters: | |
|---|---|
| Ultrasonic disintegrator: | 400 W |
| Amplitude: | 50 |
| Time: | 45 min. |

EXAMPLE 4.1

Preparation of Liposomes With Magnetically Hard Barium Hexaferrite and Strontium Hexaferrite Powders 0.8% by weight of magnetically hard barium hexaferrite powder in a thickness ratio of 6:1 and in the particle size range 600–800 nm is dispersed in 29% by weight of synthetic phospholipid and 1% by weight of lysolecithins.

| Turrax homogenizer: | 20,000 rpm |
| --- | --- |
| Time: | 7 min. |

The following substitution is possible under the same technological conditions: 0.8 percent by weight of strontium hexaferrite or a barium hexaferrite/strontium hexaferrite mixture in proportions of x% to (100-x). 10% of ethanol and qs distilled water are subsequently added.

| Turrax homogenizer: | 15,000 rpm |
| --- | --- |
| Time: | 20 min. |

EXAMPLE 4.2

Preparation of Liposomes With Magnetically Hard Barium Hexaferrite and/or Strontium Hexaferrite Powders 70% by weight of magnetically hard barium hexaferrite powder in a thickness ratio of 7:1 and in the particle size range 800–1000 nm are dispersed in 20% by weight of partially hydrogenated phospholipids and synthetic phospholipids in proportions of 1:1 and 10% by weight of lysolecithins.

| Ultrasonic disintegrator | 400 W |
| --- | --- |
| Amplitude: | 50 |
| Time: | 30 min. |

The following substitution is possible under the same technological conditions: 70% by weight of strontium hexaferrite or a barium hexaferrite/strontium hexaferrite mixture in proportions of x% to (100-x). 10% of ethanol and as distilled water are subsequently added.

| Ultrasonic disintegrator | 400 W |
| --- | --- |
| Amplitude: | 50 |
| Time: | 70 min. |

EXAMPLE 5

Preparation of Asymmetric Lamellar Aggregates With Magnetically Hard Barium Hexaferrite and/or Strontium Hexaferrite Powders 0.01% by weight of magnetically hard barium hexaferrite powder in a thickness ratio of 3:1 and in the particle size range 750–900 nm are dispersed in 8% by weight of phospholipids with a phosphatidylcholine content of 30% by weight of egg lecithin.

| Turrax homogenizer | 27,000 rpm |
| --- | --- |
| Time: | 5 min. |

The following substitution is possible under the same technological conditions: 0.01% by weight of strontium hexaferrite or a barium hexaferrite/strontium hexaferrite mixture in proportions of x% to (100-x). 6.0% by weight of glycerol, 6% by weight of propylene glycol, 0.2% by weight of oxygen-charged fluorocarbons and as distilled water are subsequently added.

| Turrax homogenizer: | 25,000 rpm |
| --- | --- |
| Time: | 20 min. |

EXAMPLE 6

Preparation of Asymmetric Lamellar Aggregates With Magnetically Hard Barium Hexaferrite and/or Strontium Hexaferrite Powders 1.0% by weight of magnetically hard barium hexaferrite powder in a thickness ratio of 10:1 and in the particle size range 800–950 nm are dispersed in 10% by weight of phospholipids with a phosphatidylcholine content of 99% by weight of soya lecithin.

| Turrax homogenizer | 27,000 rpm |
| --- | --- |
| Time: | 10 min. |

The following substitution is possible under the same technological conditions: 1.0% by weight of strontium hexaferrite or a barium hexaferrite/strontium hexaferrite mixture in proportions of x% to (100-x). 6.0% by weight of glycerol, 6% by weight of propylene glycol, 50% by weight of oxygen-charged fluorocarbons and qs distilled water are subsequently added.

| Turrax homogenizer: | 27,000 rpm |
| --- | --- |
| Time: | 20 min. |

EXAMPLE 7

Preparation of a Fluorocarbon Dispersion With Magnetically Hard Barium Hexaferrite and/or Strontium Hexaferrite Powders 4% by weight of magnetically hard barium hexaferrite powder in a thickness ratio of 4:1 and in the particle size range 850–1000 nm are dispersed in 100% by weight of oxygen-charged fluorocarbons.

| Ultrasonic disintegrator | 400 W |
| --- | --- |
| Amplitude: | 50 |
| Time: | 25 min. |

The following substitution is possible under the same technological conditions: 0.4 percent by weight of strontium hexaferrite or a barium hexaferrite/strontium hexaferrite mixture in proportions of x% to (100-x).

EXAMPLE 8

Preparation of a Fluorocarbon Dispersion With Magnetically Hard Barium Hexaferrite and/or Strontium Hexaferrite Powders 60% by weight of magnetically hard strontium hexaferrite powder in a thickness ratio of 9:1 and in the particle size range 900–1200 nm are dispersed in 100% by weight of oxygen-charged fluorocarbons.

| | |
|---|---|
| Ultrasonic disintegrator | 400 W |
| Amplitude: | 50 |
| Time: | 60 min. |

The following substitution is possible under the same technological conditions: 60% by weight of barium hexaferrite or a barium hexaferrite/strontium hexaferrite mixture in proportions of x% to (100-x).

EXAMPLE 9

Dermatological Ointment

| | |
|---|---|
| Phase A: | |
| Beeswax | 8% |
| Synthetic Lanolin | 10% |
| Phase B: | |
| Glycerol | 10% |
| Distilled H$_2$O | qs |
| Phase C: | |
| Fluorocarbon dispersion according to Example 7 | 50% |

Preparation:
Phase A is heated to 65° C., with stirring. Phase B is also heated to 65° C. and added to phase A, with stirring, the temperature remaining stable. The homogenization time is 10 minutes. This is followed by the cooling phase. When the temperature reaches ≦30° C., phase C is added, with slow stirring.

EXAMPLE 10

Dermatological Paste

| | |
|---|---|
| Phase A: | |
| Cetostearyl alcohol | 5% |
| Beeswax | 15% |
| Synthetic lanolin | 20% |
| Phase B: | |
| Propylene glycol | 5% |
| Glycerol | 5% |
| Distilled H$_2$O | qs |
| Phase C: | |
| Fluorocarbon dispersion according to Example 6 | 30% |

Preparation:
Phase A is heated to 65° C., with stirring. Phase B is also heated to 65° C. and added to phase A, with stirring, the temperature remaining stable. The homogenization time is 10 minutes. This is followed by the cooling phase. When the temperature reaches ≦30° C., phase C is added, with slow stirring.

EXAMPLE 11

Dermatological Paste

| | |
|---|---|
| Glycerol | 10% |
| Propylene glycol | 5% |
| Fluorocarbon dispersion | 85% |

The raw materials are successively mixed at room temperature.

EXAMPLE 12

Dermatological Tincture

| | |
|---|---|
| Glycerol | 5% |
| Propylene glycol | 5% |
| Water | qs |
| Suspension with magnetically hard powder according to Example 1 | 1% |

All the raw materials are mixed in water, in any chosen order, at room temperature.

EXAMPLE 13

W/O Emulsion

| | |
|---|---|
| Emulsifier system consisting of phosphoric acid ester and isopropyl palmitate in proportions of 35%:65% | 8.2% |
| Paraffin | 12.2% |
| Glycerol | 5.3% |
| Preservative | 0.3% |
| Water | qs |
| Dispersion with magnetically hard powder according to Example 5 | 10.0% |

Preparation in the cold: The raw materials are mixed in order and then homogenized for about 10 minutes.

EXAMPLE 14

O/W Emulsion

| | |
|---|---|
| Phase A: | |
| Glycerol stearate | 1.0% |
| Stearic acid | 2.0% |
| Cocoa butter | 3.0% |
| Cetyl alcohol | 1.5% |
| Oleyl alcohol | 0.5% |
| Dimethicone | 1.0% |
| Disodium EDTA | 0.15% |
| Butyl acetate/hydroxytoluene | 0.05% |
| Phase B: | |
| Distilled H$_2$O | qs |
| Carbomer | 0.5% |
| Propylene glycol | 3.5% |
| Glycerol | 2.5% |
| Preservative | 0.5% |
| Phase C: | |
| TEA | 0.5% |
| Phase D: | |
| Perfume oil | 0.5% |
| Dispersion with magnetically hard powder according to Example 5 | 5.0% |

Preparation: Phase A is heated to 80° C., with stirring. Phase B is also heated to 80° C. and added to Phase A. Then Phase C is added, and Phase D is added.

EXAMPLE 15

Cosmetic Gel

| | |
|---|---|
| Distilled water | qs% |
| Carbomer | 0.6% |
| TEA | 0.6% |
| Preservative | 0.3% |
| Propylene glycol | 3.5% |
| Glycerol | 4.0% |
| Natural oil | 2.0% |
| Perfume oil | 0.5% |
| Suspension with magnetically hard powder according to Example 2 | 2.5% |

Preparation/Preparation in the cold: The water and carbomer are homogenized at room temperature. The remaining raw materials are added in order, with stirring.

| | |
|---|---|
| Polyacrylic acid MW 4 million | 0.5% |
| Triethanolamine | 0.5% |
| Cetostearyl alcohol | 2.0% |
| Propyl glycol | 2.0% |
| Glycerol | 1.5% |
| Vitamin E | 1.0% |
| Distilled water | qs |
| Perfume oil | 0.5% |
| Preservative | 0.3% |
| Dispersion with magnetically hard powder according to Example 5 | 3.5% |

The preparation/preparation in the cold is carried out according to Example 15.

EXAMPLE 17

Hair Lotion

| | |
|---|---|
| Distilled water | qs |
| Carbomer | 0.05% |
| TEA | 0.1% |
| Vitamin B | 1.0% |
| Propylene glycol | 2.0% |
| Perfume oil | 0.5% |
| Suspension with magnetically hard powder according to Example 3 | 1.5% |

The preparation/preparation in the cold is carried out according to Example 15.

EXAMPLE 18

Hair/Scalp Pack

| | |
|---|---|
| Distilled water | qs |
| Cetyl alcohol | 3.0% |
| Phosphoric acid ester/isopropylamide 1:1 | 6.5% |
| Coconut glycerides O | 3.5% |
| Stearic acid | 6.0% |
| Glycerol | 5.0% |
| Lecithin | 1.0% |
| Liposomes according to Example 4.1 | 20.0% |

The preparation/preparation in the cold is carried out according to Example 15.

EXAMPLE 19

O/W Special Emulsion Base

| | |
|---|---|
| Phase A: | |
| Cetearyl alcohol | 1.5% |
| Cetearyl alcohol and PEG-40 castor oil in proportion of 1:1 | 3.0% |
| Hexyl laurate | 1.5% |
| Dibutyl adipate | 4.0% |
| Oleyl erucate | 1.5% |
| Phase B: | |
| Distilled water | qs |
| Carbomer | 0.3% |
| Allantoin | 0.2% |
| Phase C: | |
| TEA | 0.3% |
| Phase D: | |
| Aloe vera | 2.0% |
| Silicone Oil | 3.0% |
| D-Panthenol | 0.5% |
| Babassu oil | 2.0% |
| Vitamin A palmitate | 1.0% |
| Olive oil | 2.0% |
| Preservative | 0.3% |
| Asymmetric lamellar aggregates with magnetically hard powders | 15.0% |

The preparation is carried out according to Example 14.

EXAMPLES 20–25

The preparation samples were subjected to an application test according to Example 34 and showed the following results based on a composition of the emulsion (ointment) with respect to the basic ingredients:

EXAMPLE 20(a)

| | |
|---|---|
| Vaseline | 20% |
| Jojoba oil | 1% |
| Water | (quantum satis) qs |
| Glycerine | 3% |
| Aloe vera | 1% |
| Preservative agent | 0.5% |

Magnetically hard single domain particles (SDP) of barium hexaferite with a particle size of 600 nm and a coercive field strength of 4200 oersted were added to the composition of Example 20(a) and the microcirculation was measured.

| Example | SDP % by weight | % im[1] |
|---|---|---|
| 20 | 0.02 | 150 |
| 21 | 2 | 170 |
| 22 | 10 | 180 |
| 23 | 15 | 195 |
| 24 | 50 | 205 |
| 25 | 65 | 170 |

[1] increased microcirculation after 30 min.

EXAMPLES 26–27

At room temperature 1% Aspirin (acetylsalicylic acid) was blended into the composition of Example 20(a). The following result was obtained:

| Example | SDP % by weight | % im[1] |
| --- | --- | --- |
| 26 | 5 | 135 |
| 27 | 10 | 145 |

[1]increased microcirculation after 2 hr.

This result is an average of 5 test volunteers suffering locally induced pain through skin irritation. At the time of the measurement after two hours the pain had diminished considerably or completely.

The same composition but without Aspirins was applied to a control group. The increase in microcirculation occurred in the same manner, however, the pain only subsided after 4 to 6 hours.

EXAMPLES 28–29

The preparation samples were subjected to an application test according to Example 34. The composition of the emulsion was the same as in Example 20(a). At room temperature 2% Meloxicam was blended into this composition. The following result was obtained:

| Example | SDP % by weight | % im[1] |
| --- | --- | --- |
| 28 | 5 | 130 |
| 29 | 15 | 155 |

[1]increased microcirculation after 2 hr.

The ointment was applied to 5 test volunteers with acute rheumatic pain. After the measurement two hours later an essential pain soothing of more than 50% had occurred for all test volunteers.

EXAMPLES 30–31

The preparation samples were subjected to an application test according to Example 34. The composition of the emulsion was the same as in Example 20(a). At room temperature 4% heparin sodium was blended into this composition. The following result was obtained:

| Example | SDP % by weight | % im[1] |
| --- | --- | --- |
| 30 | 5 | 135 |
| 31 | 20 | 155 |

[1]increased microcirculation after 2 hr.

The ointment was applied to 5 test volunteers with average swellings at the joints. After the measurement of the microcirculation two hours later a further measurement of the circumference took place, in which an average reduction of the swelling of 18% could be determined.

EXAMPLES 32–33

The preparation samples were subjected to an application test according to Example 34. The composition of the emulsion was the same as in Example 20(a). At room temperature 4% E and A (1:1) vitamin mixture and 2.5% penicillin was blended into this composition. The following result was obtained:

| Example | SDP % by weight | % im[1] |
| --- | --- | --- |
| 32 | 12 | 140 |
| 33 | 30 | 168 |

[1]increased microcirculation after 2 hr.

This result is an average of 5 test volunteers who had inflammation arising from a skin irritation. At the time of the measurement after two hours the inflammation had diminished either markedly or completely.

The same composition but without the vitamin mixture and penicillin was applied to a control group. The increase in microcirculation occurred in the same manner, however the inflammation only subsided after 5 to 7 hours.

EXAMPLE 34

Cosmetic preparations produced according to Example 19 were subjected to an application test in which the microcirculation of the skin was measured after the application of a sample in the form of an ointment.

The circulation of the skin is known to be obtained from the product of the blood flow and the vascular volume. In addition to vasodilation and constriction, the capillaries are subject to a pulsating vasomotion called the capillary pulse. The microcirculation was quantitatively determined using the laser Doppler flow measurement with a Periflux apparatus (Perimet KB, Sweden). The 2 mW helium-neon laser was transmitted to the measuring point through a flexible fibre-optic light guide. The optical fibre was fixed to the measuring area by means of a holder, ensuring a depth of penetration of the laser light into the skin tissue of 1.5–2 mm. A voltage was measured as the output and input signal, which, as a relative measure of the circulation of the tissue, is directly proportional to the product of the quantity of erythrocytes and the speed of the erythrocytes. The method afforded a continuous, contact-free and quantitative recording of the circulation of the skin. As the skin temperature has a large influence on the cutaneous microcirculation or on the responsiveness of the capillaries, the environmental conditions had to be approximated to those of the physiologically indifferent areas and kept constant throughout the entire duration of the experiment. These experimental conditions for test subjects were 26° C.±36%±1 relative humidity, the test subjects having already been adapted to these conditions for thirty minutes beforehand. After a blank measurement, an excess of the ointment samples was allowed to act for thirty minutes on an area of skin on the inside of the forearm. The significance level p was <0.05.

In test subjects who responded to the ointment applied, an increase in microcirculation of up to 200% was found. FIG. 1 shows an increase in microcirculation markedly above the initial value M100 for samples containing magnetically hard single-domain particles, in this case samples M101, M102 and M103.

While several embodiments of the present invention have been shown and described, it is to be understood that many changes and modifications may be made thereunto without departing from the spirit and scope of the invention as defined in the appended claims.

What is claimed is:

1. A preparation for stimulating the blood circulation of the skin comprising a dispersion containing a proportion of finely divided magnetically hard single-domain particles in the dispersion being in the range from 0.01% to 70% by weight, based on the total weight of the dispersion; said particles having a strong coercive field and being in the range 600 to 1200 nm;

wherein the magnetically hard single-domain particles are selected from the group consisting of barium hexaferrite, strontium hexaferrite, undoped barium hexaferrite, undoped strontium hexaferrite, and the mixtures thereof; and the balance up to 100% by weight of a cosmetic or pharmaceutical excipient carrier substance or a pharmaceutical additive, based on the total weight of the dispersion.

2. A preparation according to claim 1, wherein the magnetically hard single-domain particles are barium hexaferrite.

3. A preparation according to claim 1, wherein the magnetically hard single-domain particles with a strong coercive field are selected from the group consisting of barium hexaferrite, strontium hexaferrite and the mixtures thereof.

4. A preparation according to claim 1, wherein the magnetically hard single-domain particles are in the range 750 to 1000 nm.

5. A preparation according to claim 1, wherein the magnetically hard single-domain particles are in the range 800 to 950 nm.

6. A preparation according to claim 1, further comprising a coating layer on the magnetically hard single-domain particles, said layer reduces the coercive field only slightly, and prevents the escape of barium ions and strontium ions.

7. A preparation according to claim 1, wherein said cosmetic or pharmaceutical carrier substances or pharmaceutical additives are selected from the group consisting of cytostatic agents, carcinostatic agents, immunomodulators, vaccines, virustatic agents, virucidal medicinal agents, antimycotic agents, heparins, antibiotics, corticoids, anti-infective agents, active ingredients for acne, local anaesthetics, antiphlogistics, antihistamines, antipsoriatics, non-steroidal analgesics, non-steroidal antirheumatics, opiate receptor agonists; opiate receptor antagonists, histamine antagonists, insulins, regulatory peptides and their inhibitors, sedatives, hypnotics, rosmaric acid, a virucidal active ingredient, a virustatic active ingredient occurring in plants, oligopeptides, polypeptides, vitamin E, vitamin A, vitamin B, and vitamin C, and also the pigment melanin.

8. The preparation of claim 1, wherein the magnetically hard single-domain particles have a coercive field strength in the range of 3000 to 5000 Oersted.

9. The preparation according to claim 1, wherein said excipient is selected from the group consisting of ointment, cream, lotion, cologne, alcoholic extract, paste, gel, powder, tincture, a spray being on a dressing and a spray being on a plaster.

10. A process for the manufacture of a preparation for stimulating the blood circulation of the skin comprising incorporating magnetically hard single-domain particles with a strong coercive field and with a size in the range of 600 to 1200 nm into a pharmaceutically or cosmetically acceptable excipient or additive to form a dispersion; and wherein the magnetically hard single-domain particles are selected from the group consisting of barium hexaferrite, strontium hexaferrite, undoped barium hexaferrite, undoped strontium hexaferrite, and the mixtures thereof;

with the optional addition of dispersants used to form said dispersion;

wherein said dispersion contains a proportion of magnetically hard single-domain particles in the range 0.01% to 70% by weight, based on the total weight of the dispersion; and wherein the balance up to 100% by weight is said excipient or additive, based upon the total weight of said dispersion.

* * * * *